United States Patent [19]

Szejtli et al.

[11] Patent Number: 4,623,641

[45] Date of Patent: Nov. 18, 1986

[54] METHOD OF TREATING ULCERS AND EROSIONS IN THE GASTROINTESTINAL SYSTEM USING PGI$_2$-METHYL ESTER-BETA CYCLODEXTRIN INCLUSION COMPLEXES

[75] Inventors: József Szejtli; Magdolna Szejtli née Rengei; György Cseh; István Stadler, all of Budapest, Hungary

[73] Assignee: Chinoin Gyogyszer es Vegyeszeti Termekek Gyara R.T., Budapest, Hungary

[21] Appl. No.: 774,177

[22] Filed: Sep. 9, 1985

Related U.S. Application Data

[63] Continuation of Ser. No. 623,395, Jun. 22, 1984, abandoned.

[51] Int. Cl.$^4$ .............................................. A61K 31/70
[52] U.S. Cl. .................................................... 514/58
[58] Field of Search ........................................... 514/58

[56] References Cited

U.S. PATENT DOCUMENTS

| | | | |
|---|---|---|---|
| 4,070,537 | 1/1978 | Hayashi et al. | 560/51 |
| 4,117,119 | 9/1978 | Kurono et al. | 514/58 |
| 4,232,009 | 11/1980 | Hayashi et al. | 424/180 |
| 4,351,846 | 9/1982 | Matsumoto et al. | 514/58 |

FOREIGN PATENT DOCUMENTS

| | | | |
|---|---|---|---|
| 64511 | 7/1975 | Australia | 514/58 |
| 0135415 | 10/1981 | Japan | 514/58 |

OTHER PUBLICATIONS

Stadler-Szoke et al, A Forecast for Application of Cyclodextrins in the Pharma-Industry, Proc. First Int. Symp. on Cyclodextrins, p. 377 (1981).
Whittle et al., Actions of—PGI$_2$ . . . on the Rat Gastric Mucosa, Chem. Abstracts, 89: 123544a (1978).
Szejtlip et al., Inclusion Complexes of Prostacyclin . . . with Cyclodextrin, Chem. Abstracts, 91: 62728f (1979).
Hayashi et al., Preparations Containing Prostaglandin Analogs, Chem. Abstracts, 90: 127526g (1978).

*Primary Examiner*—Ethel G. Love
*Attorney, Agent, or Firm*—Karl F. Ross; Herbert Dubno

[57] ABSTRACT

A new method is disclosed for the treatment and prevention of gastrointestinal ulcers or erosions which comprises the administration of a pharmaceutically effective amount of a PGI$_2$ methyl ester-beta cyclodextrin complex to a patient in need of said treatment wherein the amount of the PGI$_2$ methyl ester constitutes 1 to 15% by weight of the complex.

9 Claims, No Drawings

METHOD OF TREATING ULCERS AND EROSIONS IN THE GASTROINTESTINAL SYSTEM USING PGI$_2$-METHYL ESTER-BETA CYCLODEXTRIN INCLUSION COMPLEXES

CROSS-REFERENCE TO RELATED APPLICATION

This is a continuation of co-pending application Ser. No. 623,395, filed on June 22, 1984, now abandoned.

This application is related to copending U.S. application Ser. No. 942,882, now abandoned, the contents of which are expressly incorporated herein by reference.

FIELD OF THE INVENTION

The invention relates to the use of the inclusion complex of PGI$_2$-methyl ester and beta cyclodextrin (PCCD) as well as to pharmaceutical compositions containing same for the prevention and therapy of gastrointestinal ulcers or erosions.

BACKGROUND OF THE INVENTION

The formation of the inclusion complex of PGI$_2$-methyl ester with beta-cyclodextrin is a preferred way for stabilizing the PGI$_2$ methyl ester. The PGI$_2$ methyl ester content of the complex amounts to 1 to 15% by weight, preferably 3% by weight. By increasing the stability, the effect of PGI$_2$ methyl ester may be prolonged in several biological systems.

It is known that some prostacyclines have some strong gastric cytoprotective effects. See B. J. R. Whittle et al, *Prostaglandine*, Vol. 15, A55 (1978). Unfortunately the cytoprotective effect may be used therapeutically, only with difficulty, because of their chemical and biological instability. The active ingredient decomposes easily so that it has to be produced either freshly or else stored under extreme conditions.

It is also known that among other prostaglandin derivatives, the PGE$_2$ has proved to be significantly effective both in decreasing the blood loss of the gastric mucosa induced by non-steroidal antiphlogistics as well as in the therapy of peptic ulcers. The use of the PGE$_2$ is, hiowever, difficult because of its diarrhogen side effects.

OBJECT OF THE INVENTION

It is the object of the invention to provide a new method of treating and/or preventing gastrointestinal ulcers and erosions whether the ulcers or erosions be stress ulcers, peptic ulcers, or ulcers caused by the administration of non-steroidal antiphlogistic agents.

SUMMARY OF THE INVENTION

It has surprisingly been found that the stabilizing effect on prostacyclin methyl ester by beta-cyclodextrin is most pronounced when the PGI$_2$-methyl ester-beta-cyclodextrin (PCCD) complex is applied in the field of gastrointestinal cytoprotection. Additionally the PCCD has the preferred feature that it does not lose its active ingredient even over a long storage period.

No one as of yet has examined the cytoprotective effect of the prostacycline methyl ester—beta-cyclodextrin complexes. Applicants have found that the cytoprotective effect of the prostacycline methyl ester—beta cylodextrin complex is much more effective than would be expected.

According to the invention a PGI$_2$ methyl ester-beta-cyclodextrin complex (PCCD) is employed in the treatment or prevention of ulcers or erosions in the gastrointestinal tract. The content of PGI$_2$ methyl ester in the cyclodextrin inclusion complex ranges from 1 to 15%, and is preferably about 3% by weight. The PCCD may be administered to subjects per se or together with a pharmaceutically acceptable inert carrier.

The preferred method of administration to the patient is oral administration. However, the invention also contemplates administration of the PCCD by injection or by infusion.

The new method of treatment or prevention of ulcers or erosions applies to ulcers or erosions at any point in the gastrointestinal tract from any number of causes. For instance the new method is applicable to the treatment of peptic ulcers. The new method is similarly applicable to the treatment of stress ulcers. Furthermore it is wellknown that non-steroidal antiphlogistic agents such as indomethacin often cause ulcerogenic side effects in patients taking same. Accordingly another feature of the instantly claimed invention is the simultaneous administration of a pharmaceutically effective amount of a non-steroidal antiphlogistic agent together with an effective amount of the PCCD. Alternatively the PCCD may be administered at a different time from when the non-steroidal antiphlogistic agent is administered. Preferably the PCCD is administered subsequently to the administration of the non-steroidal antiphlogistic agent.

Another feature of the invention is a pharmaceutical composition containing a non-steroidal antiphlogistic agent, such as indomethacin, in combination with a pharmaceutically effective amount of the PCCD. The weight ratio of the PCCD to the non-steroidal antiphlogistic agent should range between 1:25 to 1:2500.

The following examples serve to show preparation of the compositions containing the PCCD which are used according to the instantly disclosed invention.

EXAMPLE 1

6 mg of prostacyclin methyl ester are dissolved in 2 ml of diethyl ether. Separately 194 mg of anhydrous β-cyclodextrin are dissolved in a mixture of 1 ml of a pH 8 buffer and 5.5 ml of distilled water at 30° C. and the above prostacyclin methyl ester solution is added to the solution obtained. The mixture is stirred for one hour, under a slightly reduced pressure and is then shaken for another two hours at room temperature. The solution is frozen and lyophilized. 198 mg of prostacyclin methyl ester-β-cyclodextrin complex are obtained as an amorphous, water-soluble powder, which decomposes upon heating without melting.

EXAMPLE 2

Capsule containing 0.25 mg of active ingredient

| Composition | |
|---|---|
| PGI$_2$-methyl ester-β-CD complex (containing 3% of active ingredient) | 8.4 mg |
| Colloidal silicic acid | 9 mg |
| Talc | 5 mg |
| Magnesium stearate | 15 mg |
| Lactose | 20 mg |
| Crystalline cellulose | 40 mg |
| Potato starch | 127.6 mg |
| per capsules. | |

EXAMPLE 3

The preparation of the capsules

A powder mixture is prepared by dry granulation of a mixture containing the components described in Example 2 in the given proportions. The powder mixture is homogenized and encapsulated in a standard machine to give capsules of 225 mg.

EXAMPLE 4

Tablet containing 0.25 mg of active ingredient

| Composition | |
|---|---|
| PGI$_2$-methyl ester-$\beta$-CD complex (containing 3% of active ingredient) | 8.4 mg |
| Amylopectine | 10 mg |
| Crystalline cellulose | 60 mg |
| Stearic acid | 2 mg |
| Talc | 13 mg |
| Potato starch | 321.6 mg |
| per tablets. | |

EXAMPLE 5

The preparation of tablets

Prostacyclin-methyl ester-$\beta$-cycloextrin inclusion complex, amylopectine and microcrystalline cellulose together with a corresponding quantity of potato starch are thoroughly admixed in a homogenizing machine in the proportions given in Example 4. The given quantity of stearic acid and talc is homogenized and passed through a No. 100 seave. The fine powder obtained is admixed with the homogeneous powder mixture prepared above, and the mixture obtained is converted into tablets weighing 415 mg each. If desired, the tablets obtained are transformed into dragées or coated tablets.

EXAMPLE 6

Injection (lyophilized)

An aqueous solution of the PGI$_2$-methyl ester-$\beta$-CD complex prepared according to Example 1 is filled into ampoules, so that each ampoule should contain 5 mg of the complex having an active ingredient concentration of 3%. The ampoules are then lyophilized and subsequently sealed under nitrogen. Prior to application the lyophilized powder is dissolved in a physiological sodium chloride solution up to the desired volume.

The following tests have been carried out to show the cytoprotective effects of the inclusion complex of PGI$_2$ methyl ester and beta-cyclodextrin (PCCD).

For the following tests 200–250 g female wistar rats were fasted for 24 hours before the experiment. Water was given ad libium.

A. STRESS ULCER TEST

The rats were immobilized on their backs for 24 hours. After immobilization the animals were killed, and their stomachs were prepared for ulcer analysis.

B. INDOMETHACIN-INDUCED ULCER TEST

After 24 hours' fasting 30 mg/kg of body weight of indomethacin were administered i.p. Four hours after the administration the animals were killed and their stomachs were prepared for ulcer analysis.

The abovementioned two groups were used as control.

The gastric cytoprotective effect of PCCD was tested by administering it in the following way:

Case A: At 0, 6th, 12th and 18th hour after the immobilization.

Case B: At 0 and 2nd hour after the indomethacin administration.

Administrations were carried out both ip and per os.

In both cases the animals were killed and their stomachs prepared for ulcer analysis.

In each experiment the ulcer index was calculated.

In the calculation of the U.I., each mm$^2$ of ulcer or erosion is 1 point. Bleeding results in an additional 5 points. Perforation means an additional 10 points. The number of animals is (n=20) in each group.

Mean (%)±S.E.M. is calculated. Statistical analysis is done according to the Student's T-Test. Significance level, p is less than 0.05.

TABLE A

| | STRESS ULCER TEST | |
|---|---|---|
| AGENT | U.I. ± S.E.M. | U.I. (delta %) |
| Control | 7.7. ± 2.27 | 100 |
| Beta-cyclodextrin (5 mg/kg i.p.) | 6.8 ± 2.15 | 77.9 |
| PCCD (100 micrograms/kg i.p.) | 2.3 ± 0.65* | 29.9 |
| Cimetidine (10 mg/kg i.p.) | 3.0 ± 1.08 | 38.9 |
| PGI$_2$ (100 micrograms/kg i.p.) | 5.4 ± 1.54 | 70.0 |
| PCCD (100 micrograms/kg p.o.) | 2.6 ± 1.35* | 29.0 |
| Cimetidine (10 mg/kg p.o.) | 2.82 ± 1.36 | 36.7 |

*PCCD data are calculated for active ingredient.

TABLE B

| | INDOMETHACIN-INDUCED ULCER TEST | |
|---|---|---|
| AGENT | U.I. ± S.E.M. | U.I. (Delta %) |
| Control | 7.6 ± 1.85 | 100 |
| PCCD (100 micrograms/kg i.p.) | 2.1 ± 0.59* | 27.6 |
| PCCD (100 micrograms/kg p.o.) | 2.25 ± 1.10* | 29.6 |

*PCCD data are calculated for active ingredient.

C. GASTRIC CYTOPROTECTIVE TEST

A. Robert, Prostaglandins (Suppl.), 21, 89 (1981)

The following method according to the abovementioned reference was employed:

1 ml of ethanol was administered to rats deprived of food for 24 hours orally which caused severe gastric lesions on the corpus mucosa. The cytoprotective substances were applied before giving ethanol p.o. or subcutaneously. As controls, prostacylin (PGI$_2$) and PGE$_2$ were used.

Evaluation was carried out by killing the animals and then removing their stomachs. The number of gastric lesions was determined in each case. The dose of the cytoprotective compounds giving a 50% inhibiting effect was determined. The number of gastric erosions in the stomachs of animals not treated with a cytoprotective agent was designated 100%. The results are as follows:

TABLE I

| | ED$_{50}$ (mg/kg body weight) | |
|---|---|---|
| Agent | Subcutaneously | Orally |
| PGI$_2$ | 0.04 | 1.8 |
| PGE$_2$ | 0.1 | 0.03 |

TABLE I-continued

| | ED$_{50}$ (mg/kg body weight) | |
|---|---|---|
| Agent | Subcutaneously | Orally |
| PCCD | 0.08+ | 0.24+ |

+The values of the PCCD concentration always relate to the active ingredient.

From the data in the table it can be seen that PGI$_2$ and PCCD while being administered subcutaneously have a stronger cytoprotective effect than PGE$_2$ while upon oral administration the PGI$_2$ is more unstable than is PGE$_2$ (decomposition of the prostacyclin accelerates at the acidic pH of the stomach) so according to this type of application, the PGE$_2$ proved to be more effective.

The stabilized prostacyclin (PCCD) was more effective by one order of magnitude than PGI$_2$ per se. The ratio of the ED$_{50}$ values for the two substances is respectively 0.24/1.8.

The advantage of PCCD compared with PGE$_2$ is that when administered parenterally in an amount of 100 to 300 μg/kg, there was no evidence of diarrhogen or other internal problems. Specifically the PCCD did not influence the motility of the gastrointestinal system. When administered in the doses mentioned above, the PCCD did not influence the blood pressure of anesthesized rabbits, nor did it change any of their respiratory parameters.

PCCD has proved to be a very atoxic substance. After having been administered, PCCD containing 30 mg/kg of active ingredient orally to rats of mixed sex, no death appeared after fourteen days. A further advantageous feature of the PCCD is that the amount of active ingredient contained therein does not decrease even after a long storage period, at room temperature. In view of the biological effects stated above, PCCD may be applied in the prevention or therapy of peptic ulcers, acute ulcers and other diseases of the intestines such as ulcerative colitis, Crohn disease, generalized inflammatory bowel diseases, irritable bowel syndromes, and pseudomembranous colitis as well as decreasing the blood losses caused by the ulcerogenic effects of non-steroidal antiphlogistic agents such as indomethacin.

Accordingly the PCCD may be applied together with a non-steroidal antiphlogistic agent. For example it is recommended using an indomethacin tablet containing 25–50 mg of the active ingredient together with PCCD or a PCCD preparation containing 1.0–1000 μg of active ingredient.

The PCCD may be used in the therapy of the diseases mentioned either per se or in the form of the usual pharmaceutical preparations. While preparing these preparations, known excipients, diluents, agents for adjusting the ionic strength and osmotic pressure, as well as agents for promoting the formulation and absorption may be used. The preparations obtained are solid (e.g. tablets, capsules, dragees, powders and pills), liquid (e.g. syrups, drops) or semiliquids (e.g. jellies, suspensions).

In the ulcer therapy, oral administration of the PCCD is advantageous. The necessary doses may vary between 1 microgram and 0.1 mg/kg of body weight of the patient. The precise dose depends on the particular disease and the particular patient to be treated, as well as the seriousness of the disease, the rate at which the medicament arrives at the desired body location, the special sensitivity or reactivity of the organ or patient to be treated. In any event the appropriate specific dose may be determined by those skilled in the art without the need to conduct undue experimentation.

We claim:

1. A method of treating an ulcer in a patient which comprises the step of orally administering to said patient a pharmaceutically effective amount of a PGI$_2$-methyl ester-beta-cyclodextrin complex wherein the amount of the PGI$_2$-methyl ester constitutes 1 to 15% by weight of the complex.

2. The method defined in claim 1 wherein a pharmaceutically acceptable inert carrier is combined with the PGI$_2$ methyl ester-beta cyclodextrin complex.

3. The method defined in claim 1 wherein the PGI$_2$ methyl ester-beta cyclodextrin complex is administered to treat peptic ulcers.

4. The method defined in claim 1 wherein the PGI$_2$ methyl ester-beta cyclodextrin complex is administered to the patient to treat stress ulcers.

5. The method defined in claim 1 wherein the PGI$_2$ methyl ester-beta cyclodextrin complex is administered simultaneously with or subsequent to administration of a non-steroidal antiphlogistic agent.

6. The method defined in claim 7 wherein the non-steroidal antiphlogistic agent is indomethacin.

7. In an antiphlogistic method of treatment wherein a non-steroidal antiphlogistic agent is administered to a patient in need of said treatment, the improvement which comprises the oral administration of a pharmaceutically effective amount of PGI$_2$ methyl ester-beta cyclodextrin complex simultaneously to or subsequently to the administration of the non-steroidal antiphlogistic agent, wherein the amount of the PGI$_2$ methyl ester-beta cyclodextrin complex constitutes 1 to 15% by weight of the complex.

8. An antiphlogistic composition suitable for oral administration having reduced ulcerogenic side effects which comprises:

(a) a pharmaceutically effective amount of a non-steroidal antiphlogistic agent, and (b) a pharmaceutically effective amount of a PGI$_2$ methyl ester-beta cyclodextrin complex, optionally along with a pharmaceutically acceptable inert carrier.

9. A method of preventing formation of an ulcer in a patient which comprises the step of orally administering to said patient a pharmaceutically effective amount of PGI$_2$ methyl ester-beta cyclodextrin complex wherein the amount of the PGI$_2$ methyl ester-beta cyclodextrin complex constitutes 1 to 15% by weight of the complex.

* * * * *